US012629397B2

(12) United States Patent
Park et al.

(10) Patent No.: US 12,629,397 B2
(45) Date of Patent: May 19, 2026

(54) WEISSELLA CIBARIA GSKM06 AND USE THEREOF

(71) Applicant: Greenstore Inc., Seongnam-si (KR)

(72) Inventors: Young Chang Park, Seongnam-si (KR); Dae Keun Shin, Seoul (KR); Jin Su Koo, Seoul (KR); Na Yeon Lee, Seoul (KR); Chaeyoung Bang, Seoul (KR)

(73) Assignee: Greenstore Inc., Seongnam-si (KR)

( * ) Notice: Subject to any disclaimer, the term of this patent is extended or adjusted under 35 U.S.C. 154(b) by 391 days.

(21) Appl. No.: 18/346,491

(22) Filed: Jul. 3, 2023

(65) Prior Publication Data

US 2024/0216445 A1     Jul. 4, 2024

(30) Foreign Application Priority Data

Dec. 30, 2022     (KR) ........................ 10-2022-0190903

(51) Int. Cl.
A61K 35/744          (2015.01)
A61P 37/02          (2006.01)

(52) U.S. Cl.
CPC ............ A61K 35/744 (2013.01); A61P 37/02 (2018.01)

(58) Field of Classification Search
CPC ......... A61P 37/00; A61P 37/02; A61K 35/744
See application file for complete search history.

(56) References Cited

FOREIGN PATENT DOCUMENTS

| KR | 10-2015-0031922 | A | 3/2015 |
|----|----|----|----|
| KR | 10-1783672 | B1 | 10/2017 |
| KR | 10-2018-0054029 | A | 5/2018 |
| KR | 10-2018-0059728 | A | 6/2018 |
| KR | 10-1873393 | B1 | 7/2018 |
| KR | 10-1937364 | B1 | 1/2019 |
| KR | 10-2330010 | B1 | 11/2021 |
| KR | 10-2390755 | B1 | 4/2022 |
| KR | 10-2022-0093990 | A | 7/2022 |
| WO | WO-2020122448 | A1 * | 6/2020 ........... A61K 35/744 |

OTHER PUBLICATIONS

Buelow et al., Medscape, 2024; https://emedicine.medscape.com/article/136217-treatment?form=fpf, (Year: 2024).*

Santos-Longhurst, Heathline.com; 2024, https://www.healthline.com/health/chronic-inflammation#:~:text=Inflammation%20refers%20to%20your%20body's,response%20from%20your%20immune%20system (Year: 2024).*

Kyung-Hyo Do et al., "Therapeutic Efficacy of Weissella cibaria CMU and CMS1 on Allergic Inflammation Exacerbated by Diesel Exhaust Particulate Matter in a Murine Asthma Model", Medicina, 2022, pp. 1-12, vol. 58, Article No. 1310.

Min-Jeong Kim et al., "Weissella cibaria CMU exerts an anti-inflammatory effect by inhibiting Aggregatibacter actinomycetemcomitans-induced NF-κB activation in macrophages", Molecular Medicine REPORTS, 2020, pp. 4143-4150, vol. 22.

Jinsu Koo et al., "Safety evaluation of Lactobacillus plantamm and Weissella cibaria strain isolated from pear and Korean melon to use as a dietary probiotics additives", Poster Presentation in 2022 KFN International Symposium and Annual Meeting, Oct. 19-21, 2022, 6 pages.

Ji-Eun Yeu, et al., "Antimicrobial and Antibiofilm Activities of Weissella cibaria against Pathogens of Upper Respiratory Tract Infections," Microorganisms 2021, vol. 9, No. 1181, pp. 1-13 (13 pages total).

Office Action issued Jul. 2, 2024 in Korean Application No. 10-2022-0190903.

* cited by examiner

*Primary Examiner* — Brian Gangle
*Assistant Examiner* — Lakia J Jackson-Tongue
(74) *Attorney, Agent, or Firm* — Sughrue Mion, PLLC

(57)          ABSTRACT

Disclosed are a *Weissella cibaria* GSKM06 strain and the use thereof. The strain is safe because it has no toxicity to the human body and has excellent physiological activities such as suppression of inflammatory reactions as well as immunomodulatory effects, thus being useful as a substance to treat immune hypersensitivity (allergic diseases such as skin, asthma and rhinitis), normalize immunity, and prevent, ameliorate or treat inflammatory diseases.

2 Claims, 12 Drawing Sheets

Specification includes a Sequence Listing.

PlasmidFinder-2.0 Server-Results

Organism(s): *Gram Positive*

Inc18

| Plasmid | Identity | Query/Template length | Contig | Position in contig | Note | Accession number |
|---|---|---|---|---|---|---|
| No hit found | | | | | | |

RepL

| Plasmid | Identity | Query/Template length | Contig | Position in contig | Note | Accession number |
|---|---|---|---|---|---|---|
| No hit found | | | | | | |

Rep1

| Plasmid | Identity | Query/Template length | Contig | Position in contig | Note | Accession number |
|---|---|---|---|---|---|---|
| No hit found | | | | | | |

Rep2

| Plasmid | Identity | Query/Template length | Contig | Position in contig | Note | Accession number |
|---|---|---|---|---|---|---|
| No hit found | | | | | | |

Rep_trans

| Plasmid | Identity | Query/Template length | Contig | Position in contig | Note | Accession number |
|---|---|---|---|---|---|---|
| No hit found | | | | | | |

RepA_N

| Plasmid | Identity | Query/Template length | Contig | Position in contig | Note | Accession number |
|---|---|---|---|---|---|---|
| No hit found | | | | | | |

NT_Rep

| Plasmid | Identity | Query/Template length | Contig | Position in contig | Note | Accession number |
|---|---|---|---|---|---|---|
| No hit found | | | | | | |

Rep3

| Plasmid | Identity | Query/Template length | Contig | Position in contig | Note | Accession number |
|---|---|---|---|---|---|---|
| No hit found | | | | | | |

Home    Services    Instructions    Output extended output

FIG. 1

SEQUENCE LISTING

```
Sequence total quantity: 2
SEQ ID NO: 1           moltype = DNA  length = 1443
FEATURE                Location/Qualifiers
source                 1..1443
                       mol_type = genomic DNA
                       organism = Weissella cibaria
SEQUENCE: 1
tgctagtcga acgctttgtg gttcaactga tttgaagagc ttgctcagat atgacgatgg   60
acattgcaaa gagtggcgaa cgggtgagta acacgtggga aacctacctc ttagcaggga  120
ataacatttg gaaacagatg ctaataccgt ataacaatag caaccgcatg gttgctactt  180
aaaagatggt tctgctatca ctaagagatg gtcccgcggt gcattagtta gttggtgagg  240
taatggctca ccaagacgat gatgcatagc cgagttgaga gactgatcgg ccacaatggg  300
actgagacac ggcccatact cctacggagg cagcagtag ggaatcttcc acaatgggcg  360
aaagcctgat ggagcaacgc cgcgtgtgtg atgaagggtt tcggctcgta aaacactgtt  420
gtaagagaag aagacattga gagaacgttc aaggtgacgg acttaccaga aaggaacggc  480
taaatacgtg ccagcagccg cggtaatacg tatgttccaa gcgttatccg gatttattgg  540
gagtaaagcg agcgcagacg gttatttaag tctgaagtga aagccctcag ctcaactgag  600
gaattgcttt ggaaactgga tgacttgagt gcagtagagg aaagtggaac tccatgtgta  660
gcggtgaaat gcgtagatat atggaagaac accagtggcg aaggcggctt tctggactgt  720
aactgacgtt gaggctcgaa agtgtgggta gcaaacagga ttagataccc tggtagtcca  780
caccgtaaac gatgagtgct aggtgtttga gggtttccgc ccttaagtgc cgcagctaac  840
gcattaagca ctccgcctgg ggagtacgac cgcaaggttg aaactcaaag gaattgacgg  900
ggacccgcac aagcggtgga gcatgtggtt taattcgaag caacgcgaag aaccttacca  960
ggtcttgaca tcccttgaca actccagaga tggagcgttc ccttcgggga caaggtgaca 1020
ggtggtgcat ggttgtcgtc agctcgtgtc gtgagatgtt gggttaagtc ccgcaacgag 1080
cgcaaccctt attactagtt gccagcattc agttgggcac tctagtgaga ctgccggtga 1140
caaaccggag gaaggtgggg atgacgtcaa atcatcatgc cccttatgac ctgggctaca 1200
cacgtgctac aatggcgtat acaacgagtt gccaacccgc gagggtgagc taatctctta 1260
aagtacgtct cagttcggat tgtaggctgc aactcgccta catgaagtcg gaatcgctag 1320
taatcgcgga tcagcacgcc gcggtgaata cgttcccggg tcttgtacac accgcccgtc 1380
acaccatgag agtttgtaac acccaaagcc ggtggggtaa ccttcgggag ccagccgtct 1440
aat                                                                1443

SEQ ID NO: 2           moltype = DNA  length = 1440
FEATURE                Location/Qualifiers
source                 1..1440
                       mol_type = genomic DNA
                       organism = Lactobacillus plantarum
SEQUENCE: 2
tgcagtcgaa cgaactctgg tattgattgg tgcttgcatc atgatttaca tttgagtgag   60
tggcgaactg gtgagtaaca cgtgggaaac ctgcccagaa gcgggggata acacctggaa  120
acagatgcta ataccgcata acaacttgga ccgcatggtc cgagtttgaa agatggcttc  180
ggctatcact tttggatggt cccgcggcgt attagctaga tggtggggta acggctcacc  240
atggcaatga tacgtagccg acctgagagg gtaatcggcc acattgggac tgagacacgg  300
cccaaactcc tacgggaggc agcagtaggg aatcttccac aatggacgaa agtctgatgg  360
agcaacgccg cgtgagtgaa gaagggtttc ggctcgtaaa actctgttgt taaagaagaa  420
catatctgag agtaactgtt caggtattga cggtatttaa ccagaaagcc acggctaact  480
```

-continued

```
acgtgccagc agccgcggta atacgtaggt ggcaagcgtt gtccggattt attgggcgta   540
aagcgagcgc aggcggtttt ttaagtctga tgtgaaagcc ttcggctcaa ccgaagaagt   600
gcatcggaaa ctgggaaact tgagtgcaga agaggacagt ggaactccat gtgtagcggt   660
gaaatgcgta gatatatgga agaacaccag tggcgaaggc ggctgtctgg tctgtaactg   720
acgctgaggc tcgaaagtat gggtagcaaa caggattaga taccctggta gtccataccg   780
taaacgatga atgctaagtg ttggaggggtt tccgcccttc agtgctgcag ctaacgcatt   840
aagcattccg cctggggagt acggccgcaa ggctgaaact caaaggaatt gacgggggcc   900
cgcacaagcg gtggagcatg tggtttaatt cgaagctacg cgaagaacct taccaggtct   960
tgacatacta tgcaaatcta agagattaga cgttcccttc ggggacatgg atacaggtgg  1020
tgcatggttg tcgtcagctc gtgtcgtgag atgttgggtt aagtcccgca acgagcgcaa  1080
cccttattat cagttgccag cattaagttg ggcactctgg tgagactgcc ggtgacaaac  1140
cggaggaagg tggggatgac gtcaaatcat catgcccctt atgacctggg ctacacacgt  1200
gctacaatgg atggtacaac gagttgcgaa ctcgcgagag taagctaatc tcttaaagcc  1260
attctcagtt cggattgtag gctgcaactc gcctacatga agtcggaatc gctagtaatc  1320
gcggatcagc atgccgcggt gaatacgttc ccgggccttg tacacaccgc ccgtcacacc  1380
atgagagttt gtaacaccca aagtcggtgg ggtacacctt ttaggaacca gccgcctaat  1440
```

WEISSELLA CIBARIA GSKM06 AND USE THEREOF

CROSS REFERENCE TO RELATED APPLICATIONS

This application is claiming priority based on Korean Patent Application No. 10-2022-0190903 filed Dec. 30, 2022, the contents of all of which are incorporated herein by reference in their entirety.

INCORPORATION BY REFERENCE OF SEQUENCE LISTING

The content of the electronically submitted sequence listing, file name: Q288746_sequence listing as filed. XML; size: 5,714 bytes; and date of creation: Jul. 2, 2023, filed herewith, is incorporated herein by reference in its entirety.

BACKGROUND OF THE INVENTION

Field of the Invention

The present invention relates to a *Weissella cibaria* GSKM06 strain and the use thereof.

Description of the Related Art

Immune hypersensitivity refers to a phenomenon in which an excessive immune response occurs and is classified into an immunity-associated disease along with immune deficiency, autoimmunity, and transplantation rejection.

In accordance with the Gell & Coombs classification system, hypersensitivity reactions may be classified into four types. Based on the immunological mechanism of each disease, hypersensitivity reactions are classified into type 1 allergy, which is called "immediate hypersensitivity", because it is the most common allergy and causes anaphylaxis, type 2 allergy, which is an antibody-mediated hypersensitivity, type 3 allergy which is caused by immune complexes, and type 4 allergy which is caused by acquired immunity.

Thereamong, type 1 allergy, which is a general allergy, causes the main symptoms by mast cells and IgE among antibodies. Progenitor cells of mast cells are not yet known, but are high likely to be basophils among white blood cells. IgE bound to mast cells cannot perform an immune action against a single antigen, like a chemical substance, or an antigen that is not recognized as an antigen for various reasons, although complex binds thereto. However, a multivalent antigen having a specific sequence induces intracellular degranulation by stimulating mast cells.

This causes the release of several signaling chemicals, including histamine, leukotriene, prostaglandin and IL-4. Histamine increases the permeability of the blood vessels and releases bodily fluids from the blood vessels, causing inflammation. The release of bodily fluids causes blood pressure to decrease. Blood pressure is affected by three factors, namely, the amount of blood, the size of blood vessels, and the force of contraction of the heart. The release of bodily fluids affects blood pressure.

In addition, anaphylactic shock, which is an acute hypersensitivity reaction, causes vasodilation and airway obstruction, which are life-threatening symptoms and thus require immediate epinephrine injection and cardiopulmonary resuscitation (CPR). In addition, anaphylactic shock results in increased mucus, increased release of inflammatory bodily fluids, and increased bronchial inflammation, which may cause respiratory distress. In addition to histamine, leukotrienes increase the effects of histamine, prostaglandins act extensively on the immune response, and interleukin 4 promotes the activity of immune cells that induce IgE production. In addition, interleukin 4 promotes emigration of other leukocytes to induce chronic inflammation.

Type 1 allergy is divided into atopic and non-atopic types depending on the influence of IgE. In addition, the non-atopic type causes allergy despite low IgE levels.

Since there are histamine receptors in the stomach, gastritis symptoms may also be observed therein. In order to suppress symptoms, antihistamines, which inhibit binding of histamine to receptors to cause symptoms, and anti-inflammatory drugs, which inhibit or interfere with the prostaglandin synthesis mechanism commonly called "COX cycle" to suppress inflammation, are mainly used.

The present invention provides a novel strain having effects of ameliorating and treating immune hypersensitivity and inflammation caused thereby.

PRIOR ART LITERATURE

Patent Literature

Korean Patent No. 10-1937364 (Jan. 4, 2019) discloses a novel lactic acid bacteria derived from the human digestive tract having immunomodulatory activity and the use thereof.

Korean Patent No. 10-1783672 (Sep. 26, 2017) discloses a strain isolated from infant feces and a method for producing fermented milk having antioxidant and immune-enhancing functions using the same.

SUMMARY OF THE INVENTION

Therefore, the present invention has been made in view of the above problems, and it is an object of the present invention to provide a *Weissella cibaria* GSKM06 strain and the use thereof.

In accordance with the present invention, the above and other objects can be accomplished by the provision of a *Weissella cibaria* GSKM06 (KCTC15129BP) strain.

In accordance with another aspect of the present invention, provided is a pharmaceutical composition for preventing or treating immune hypersensitivity or an inflammatory disease containing a *Weissella cibaria* GSKM06 (KCTC15129BP) strain.

The *Weissella cibaria* GSKM06 (KCTC15129BP) strain may be selected from viable cells, dead cells, cultures and strain extracts of *Weissella cibaria* GSKM06 (KCTC15129BP).

The immune hypersensitivity may be caused by an allergen.

The inflammatory disease may be caused by immune hypersensitivity.

In accordance with another aspect of the present invention, provided is a food composition for ameliorating immune hypersensitivity an or inflammatory disease containing a *Weissella cibaria* GSKM06 (KCTC15129BP) strain as an active ingredient.

In accordance with another aspect of the present invention, provided is a food composition for improving immunity containing a *Weissella cibaria* GSKM06 (KCTC15129BP) strain as an active ingredient.

The *Weissella cibaria* GSKM06 (KCTC15129BP) strain may be selected from viable cells, dead cells, cell cultures, and strain extracts of *Weissella cibaria* GSKM06 (KCTC15129BP).

In accordance with another aspect of the present invention, provided is a health functional food for improving immunity containing a *Weissella cibaria* GSKM06 (KCTC15129BP) strain as an active ingredient.

The *Weissella cibaria* GSKM06 (KCTC15129BP) strain may be selected from viable cells, dead cells, cell cultures, and strain extracts of *Weissella cibaria* GSKM06 (KCTC15129BP).

BRIEF DESCRIPTION OF THE DRAWINGS

The above and other objects, features, and other advantages of the present invention will be more clearly understood from the following detailed description taken in conjunction with the accompanying drawings, in which:

FIG. 1 shows the result of determination as to whether or not the lactic acid bacterium of the present invention, namely, the *Weissella cibaria* GSKM06 strain has mediating horizontal genes highly related to lateral transfer using a PlasmidFinder 2.0 analysis program;

FIG. 12 shows the result of determination as to the effect of administration of the lactic acid bacteria according to the

Figure 2:
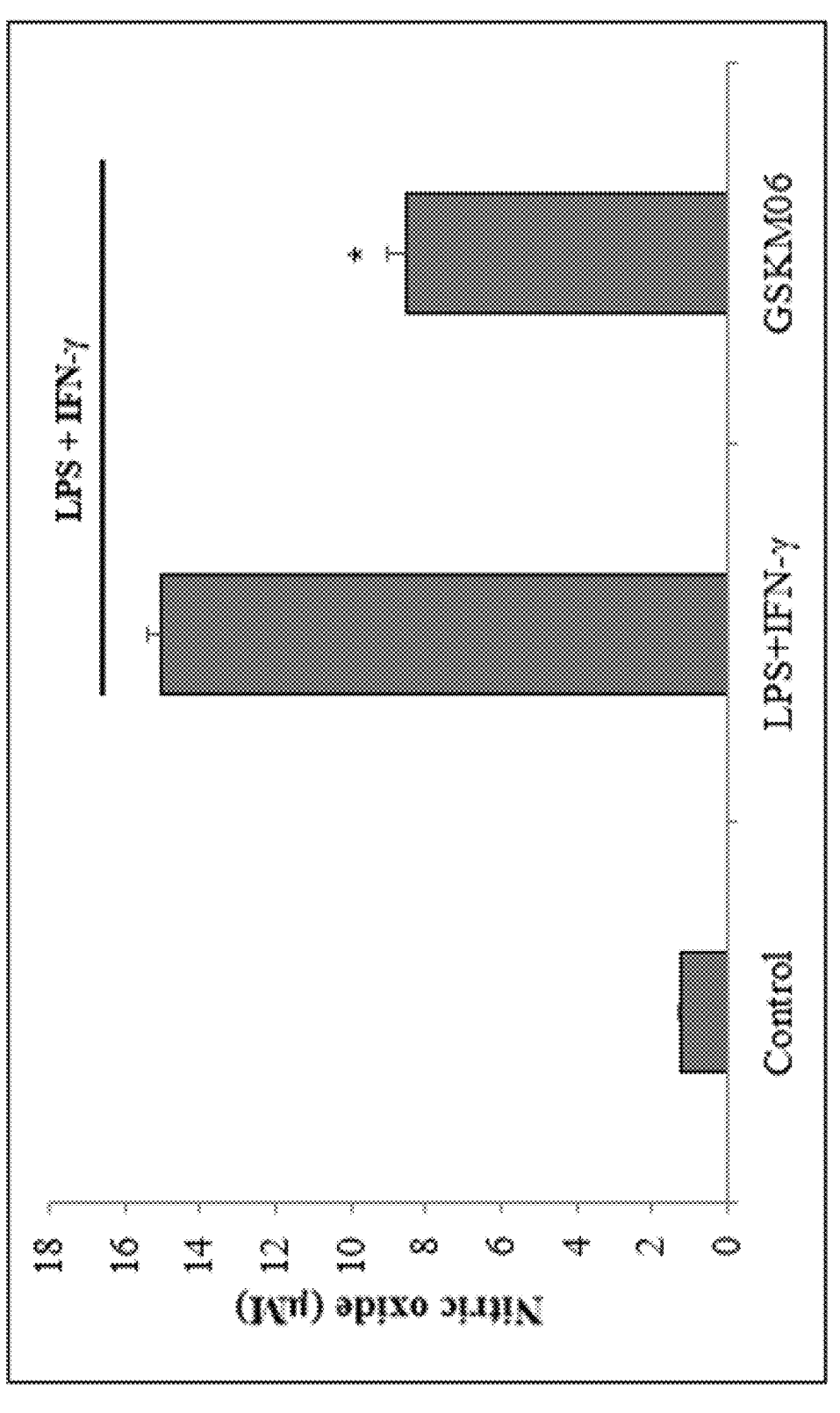
FIG. 2 shows the result of determination as to the ability of the lactic acid bacteria (*W. cibaria* GSKM06) according to the present invention to inhibit nitric oxide (NO) production.

4 present invention (*W. cibaria* GSKM06) to the airway inflammation-induced group on reduction of TNF-α.

DETAILED DESCRIPTION OF THE INVENTION

Description of overlapping contents is avoided in order to prevent confusion of the overlapping contents. That is, the following description should not be construed as limiting the scope of the present invention and the present invention should be interpreted based on the overall content of the invention.

The present invention provides a *Weissella cibaria* GSKM06 (KCTC15129BP) strain.

In an embodiment of the present invention, the strain discovered in the present invention is effective in improving immunity (increasing immunity), and ameliorating or treating immune hypersensitivity and inflammatory diseases.

Therefore, in the present invention, the strain was called "*Weissella cibaria* GSKM06" and was deposited under the accession number KCTC15129BP on Oct. 11, 2022 in the Korea Research Institute of Bioscience and Biotechnology.

Meanwhile, the present invention provides a pharmaceutical composition for preventing or treating immune hypersensitivity or an inflammatory disease containing a *Weissella cibaria* GSKM06 (KCTC15129BP) strain.

At this time, the *Weissella cibaria* GSKM06 (KCTC15129BP) strain is preferably selected from viable cells, dead cells, cell cultures, and strain extracts of *Weissella cibaria* GSKM06 (KCTC15129BP).

Immune hypersensitivity is preferably caused by an allergy-causing substance (allergen, antigen) and examples of the allergy include seasonal allergies derived from substances such as trees, grass, ragweed, and pollen, drug allergies, food allergies, allergies caused by contact with perennial allergenic antigens or specific substances (antigens) caused by dust, animal dander or mold inhalation, anaphylaxis caused by insect bites or stings, and allergies caused by infection with pathogenic bacteria.

In general, allergy causes symptoms such as sneezing, tears, itchy eyes, nasal mucus, itchy skin, and a rash. An allergic reaction, called "anaphylaxis", may be life-threatening.

In general, the immune system including antibodies, white blood cells, mast cells, complement proteins, and other substances protects the body from foreign substances (antigens). However, the immune system of vulnerable people may overreact upon exposure to certain substances (allergens) in foods, drugs or the environment that are harmless to most people.

In many allergic reactions, when the immune system is first exposed to an antigen, it produces an antibody called "immunoglobulin E (IgE)". IgE binds to white blood cells called "basophils" present in the bloodstream and to similar cells called "mast cells" present in tissues. Upon initial exposure, human body may be sensitized to the allergen, but had no symptoms.

When a sensitized person is exposed to an allergen, basophils containing IgE and mast cells release substances such as histamine, prostaglandin, and leukotrienes, which cause swelling or inflammation of surrounding tissues. Such substances initiate a series of reactions, thus continuously irritating and causing damage to tissue.

The examples of the present invention demonstrated that the strain according to the present invention effectively inhibited immune hypersensitivity and inflammation by pathogenic bacteria and drugs.

The strain according to the present invention is found to have inhibitory activity against *Moraxella catarrhalis* KCCM 42706, which is a harmful bacterium that may infect the respiratory tract, central nervous system, and human joints.

Accordingly, the immune hypersensitivity may include any one selected from respiratory infections including asthma, rhinitis and pneumonia, central nervous system infections, arthritis, sepsis, meningitis, and dermatitis.

In addition, the inflammatory disease is preferably caused by immune hypersensitivity, and examples of the inflammatory disease include sore throat, tonsillitis, epiglottitis, laryngeal bronchitis, hepatitis, esophagitis, gastritis, dermatitis, arthritis, enteritis, vaginitis, pneumonia, cholangitis, cholecystitis, and pancreatitis. There is no limitation as to the inflammatory disease so long as the inflammation is caused by an allergen.

As used herein, the term "prevention" refers to any action that suppresses or delays the onset of diseases, that is, immune hypersensitivity or inflammatory diseases, affected by administration of a pharmaceutical composition according to the present invention.

As used herein, the term "treatment" refers to any action that ameliorates or positively changes immune hypersensitivity or inflammatory diseases by administration of a pharmaceutical composition according to the present invention.

The composition containing the *Weissella cibaria* GSKM06 (KCTC15129BP) strain of the present invention as an active ingredient may further contain at least one active ingredient exhibiting the same or similar functions, in addition to the ingredient.

The pharmaceutical composition of the present invention may further contain a pharmaceutically acceptable carrier, in addition to the *Weissella cibaria* GSKM06 (KCTC15129BP) strain.

The type of carrier that can be used in the present invention is not particularly limited and any carrier commonly used in the art may be used. Non-limiting examples of the carrier include lactose, dextrose, sucrose, sorbitol, mannitol, saline, sterile water, Ringer's solution, buffered saline, albumin injection solution, xylitol, erythritol, maltitol, maltodextrin, glycerol, ethanol, and the like. These may be used alone or in combination of two or more thereof.

In addition, the pharmaceutical composition of the present invention may further contain other pharmaceutically acceptable additives such as antioxidants, excipients, diluents, buffers or bacteriostats, if necessary, and may further contain surfactants, binders, fillers, extenders, wetting agents, disintegrants, dispersants or lubricants.

The *Weissella cibaria* GSKM06 (KCTC15129BP) strain may be contained in the pharmaceutical composition n of the present invention in an amount of 0.00001 wt % to 99.99 wt %, preferably 0.1 wt % to 90 wt %, more preferably 0.1 wt % to 70 wt %, even more preferably 0.1 wt % to 50 wt %, based on the total weight of the pharmaceutical composition, but is not limited thereto, and the content of the *Weissella cibaria* GSKM06 (KCTC15129BP) strain may vary depending on the condition of the subject to whom the composition is administered, the type of specific disease, the degree of progression of the disease, and the like. If necessary, the *Weissella cibaria* GSKM06 (KCTC15129BP) strain may be present in an amount equal to the total amount of the pharmaceutical composition.

That is, the pharmaceutically effective amount and effective dosage of the pharmaceutical composition of the present invention may vary depending on the formulation method, administration method, administration time, and/or route of administration of the pharmaceutical composition, and may vary depending on several factors including the type and extent of the reaction that is achieved by administration of the pharmaceutical composition, the type, age, weight, general health condition, symptoms or severity of disease, gender, diet and excretion, of the subject to whom the composition is administered, and the ingredients of drug or other compositions administered simultaneously or sequentially to the subject, and the like, and similar factors well known in the pharmaceutical field. Those skilled in the art can easily determine and prescribe an effective dosage for the desired treatment. For example, the daily dose of the pharmaceutical composition of the present invention is about 0.01 to 1,000 mg/kg, preferably 0.1 to 100 mg/kg, and may be administered once a day or several times a day, divided into multiple doses.

The pharmaceutical composition of the present invention may be administered once a day or several times a day, divided into multiple doses. The pharmaceutical composition of the present invention may be administered as a single therapeutic agent or in combination with other therapeutic agents, sequentially or simultaneously with conventional therapeutic agents. Taking into consideration these factors, it is important to administer the composition in the minimum amount sufficient to achieve maximum efficacy without side effects, which can be easily determined by those skilled in the art.

The pharmaceutical composition of the present invention may be used in combination with various methods such as hormone therapy and drug therapy to prevent or treat immune hypersensitivity or inflammatory diseases.

As used herein, the term "administration" means supplying the pharmaceutical composition of the present invention to a patient using any suitable method. The route and mode of administration of the pharmaceutical composition of the present invention may be independent and any route and mode of administration may be used without particular limitation as long as the pharmaceutical composition can reach the desired site.

The pharmaceutical composition may be administered in an oral or parenteral administration mode and may be prepared and used in various formulations suitable for oral administration or parenteral administration.

Non-limiting examples of formulations for oral administration using the pharmaceutical composition of the present invention include oily suspensions, troches, lozenges, tablets, aqueous suspensions, prepared powders, granules, emulsions, hard capsules, soft capsules, syrups, elixirs, or the like.

In order to formulate the pharmaceutical composition of the present invention for oral administration, a binder such as sorbitol, mannitol, starch, amylopectin, cellulose, lactose, saccharose or gelatin, a lubricant such as magnesium stearate, calcium stearate, sodium stearyl fumarate or polyethylene glycol wax, an excipient such as dicalcium phosphate, a disintegrant such as corn starch or sweet potato starch, a fragrance, syrup, sweetener or the like may be used. Furthermore, in the case of capsules, in addition to the above-mentioned substances, a liquid carrier such as fatty oil may be further used.

The parenteral administration of the pharmaceutical composition of the present invention may be carried out by intramuscular administration, transdermal administration, intravenous administration, intraperitoneal administration, or subcutaneous administration, and the composition may be applied, sprayed, or inhaled to a diseased site, but parenteral administration is not limited thereto.

Non-limiting examples of parenteral preparations using the pharmaceutical composition of the present invention include injections, suppositories, ointments, powders for application, oils, powders for respiratory inhalation, aerosols for sprays, creams, and the like.

In order to formulate the pharmaceutical composition of the present invention for parenteral administration, sterile aqueous solutions, non-aqueous solvents, suspensions, emulsions, lyophilizates, external preparations, and the like may be used. The non-aqueous solvents and suspensions may include vegetable oils such as olive oil, injectable esters such as propylene glycol, polyethylene glycol, ethyl oleate and the like.

When the pharmaceutical composition of the present invention is formulated as an injection solution, it is obtained by mixing the pharmaceutical composition with a stabilizer or buffer in the presence of water to prepare a solution or suspension and injecting the solution or suspension into a unit container such as an ampoule or vial.

When the pharmaceutical composition of the present invention is formulated as an aerosol, a propellant or the like may be blended with an additive so as to disperse the water-dispersed concentrate or wet powder.

When the pharmaceutical composition of the present invention is formulated as an ointment, oil, cream, powder for application, external preparation for skin, or the like, an animal oil, vegetable oil, wax, paraffin, polyethylene glycol, silicone, bentonite, silica, talc, starch, tragacanth, cellulose derivatives, or zinc oxide may be used as the carrier ingredient.

Meanwhile, the present invention provides a food composition for ameliorating immune hypersensitivity or an inflammatory disease containing a *Weissella cibaria* GSKM06 (KCTC15129BP) strain as an active ingredient.

Also, the present invention provides a food composition for improving immunity containing a *Weissella cibaria* GSKM06 (KCTC15129BP) strain as an active ingredient.

The *Weissella cibaria* GSKM06 (KCTC15129BP) strain may be selected from viable cells, dead cells, cell cultures, and strain extracts of *Weissella cibaria* GSKM06 (KCTC15129BP).

As used herein, the term "amelioration" refers to any action that positively or beneficially changes immunity, immune hypersensitivity or an inflammatory disease by administration of the pharmaceutical composition according to the present invention.

The *Weissella cibaria* GSKM06 (KCTC15129BP) strain is preferably contained in the pharmaceutical composition of the present invention in an amount of 0.00001 wt % to 50 wt %, based on the total weight of the pharmaceutical composition. When the content of the *Weissella cibaria* GSKM06 (KCTC15129BP) strain is less than 0.00001% by weight, the effect thereof is insufficient, and when the content thereof is higher than 50% by weight, the increase in effect compared to the amount used is insufficient, which is uneconomical.

The food composition of the present invention may be, for example, any one selected from noodles, gums, dairy products, ice cream, meat, grains, caffeinated beverages, general drinks, chocolate, bread, snacks, confectionery, candy, pizza, jellies, alcoholic beverages, alcohol, vitamin complexes and other health supplements, but is not limited thereto.

When the food composition of the present invention is used in the form of a food additive, it may be added alone or used in combination with other food or food ingredients, and may be appropriately used according to a conventional method.

Meanwhile, the present invention provides a health functional food for improving immunity containing a *Weissella cibaria* GSKM06 (KCTC15129BP) strain as an active ingredient.

The improvement of immunity means amelioration of immunity.

The *Weissella cibaria* GSKM06 (KCTC15129BP) strain may be selected from viable cells, dead cells, cell cultures, and strain extracts of *Weissella cibaria* GSKM06 (KCTC15129BP).

The term "health functional food" means food manufactured and processed using raw materials or ingredients useful for the human body according to Health Functional Food Act No. 6727, and the term "functional" means intake of food with the goal of obtaining beneficial effects for health such as regulation of nutrients appropriate for structures and functions of the human body or for health applications such as physiological effects.

The food composition or health functional food of the present invention may contain additional ingredients that are commonly used to improve odor, taste, appearance, and the like. For example, the food composition may contain biotin, folate, pantothenic acid, vitamins A, C, D, E, B1, B2, B6, and B12, niacin, and the like. For example, the food composition or health functional food may contain minerals such as chromium (Cr), magnesium (Mg), manganese (Mn), copper (Cu), zinc (Zn), iron (Fe), and calcium (Ca). In addition, the food composition may contain amino acids such as cysteine, valine, lysine, and tryptophan. In addition, the food composition or health functional food may contain food additives such as preservatives (such as potassium sorbate, sodium benzoate, salicylic acid, and sodium dehydroacetate), coloring agents (such as tar pigments), coloring agents (such as sodium nitrite and sodium nitrite), bleach (sodium sulfite), disinfectants (such as bleaching powder and high-grade bleaching powder, and sodium hypochlorite), expanders (such as alum, D-potassium hydrogen tartrate), reinforcements, emulsifiers, thickeners, coating agents, antioxidants (such as butylhydroxyanisole (BHA) and butylhydroxytoluene (BHT)), seasonings (such as MSG), sweeteners (such as dulcin, cyclamate, saccharin, and sodium), flavorings (such as vanillin and lactones), gum bases, foam inhibitors, solvents, enhancers, and the like. The food additives may be selected depending on the type of food and used in an appropriate amount.

The content of the *Weissella cibaria* GSKM06 (KCTC15129BP) strain in the health functional food of the present invention is not particularly limited and may be varied depending on the condition of the subject to whom the food is administered, the type of specific disease, the degree of progression, and the like. If necessary, the content of the *Weissella cibaria* GSKM06 (KCTC15129BP) strain may be equal to the total content of food.

Hereinafter, the present invention will be described in more detail with reference to the following examples and experimental examples. However, the scope of the present invention is not limited to the examples and experimental examples and includes variations and technical concepts equivalent thereto.

Example 1: Isolation and Identification of *Weissella cibaria* (*W. cibaria*) GSKM06

1. Isolation of Lactic Acid Bacteria

Korean melons harvested in season at a farm in Seongju were prepared in MRS liquid medium [Lactobacilli MRS broth; Difco, USA] and pre-incubated at 37° C. for about 48 hours. Then, the culture medium was thoroughly diluted using a sterile diluent (3M, USA) and cultured aerobically at 37° C. in BCP medium prepared by adding 0.05% of bromocresol purple to MRS agar medium (Lactobacilli MRS agar; Difco, USA) for about 48 hours, and pure isolation was performed. The nucleotide sequence information of the entire genome of the finally isolated strain was identified using WGS (whole-genome sequencing).

2. Identification of Lactic Acid Bacteria

The species of the strain isolated from the melons was identified by gram staining, physiological characteristics, 16S rRNA sequence, and the like, and the name of the strain was assigned. The lactic acid bacteria was identified as a "*Weissella cibaria* strain" and named "*Weissella cibaria* GSKM06". The 16S rRNA sequence of *Weissella cibaria* GSKM06 is defined by SEQ ID NO: 1.

3. Characterization of Sugar Metabolism

Sugar metabolisms were characterized using the API 50CHL kit (Bio Merioux, France) in accordance with the experimental method of the manufacturer. As can be seen from Table 1 below, as a result of the characterization of sugar metabolism of the strain isolated above, *Weissella cibaria* was identified and the result of identification based on sequencing of the 16s rRNA gene was verified again.

TABLE 1

| Carbon source | Strain name W. cibaria GSKM06 |
| --- | --- |
| Control | – |
| Glycerol | – |
| Erythritol | – |
| D-arabinose | – |
| L-arabinose | + |
| D-ribose | – |
| D-xylose | + |
| L-xylose | – |
| D-xylose | – |
| Methyl-beta-D-xylopyranoside | – |
| D-galactose | – |
| D-glucose | + |
| D-fructose | + |
| D-mannose | + |
| L-sorbose | – |
| L-rhamnose | – |
| Dulcitol | – |
| Inositol | – |
| D-mannitol | – |
| D-sorbitol | – |
| Methyl-alpha-D-mannopyranoside | – |
| Methyl-alpha-D-glucopyranoside | – |
| N-acetylglucosamine | + |
| Amygdalin | + |
| Arbutin | + |
| Esculin ferric citrate | + |
| Salicin | + |
| D-cellobiose | + |
| D-maltose | + |
| D-lactose (bovine origin) | – |
| D-melibiose | – |
| D-saccharose (sucrose) | + |
| D-trehalose | – |

TABLE 1-continued

| Carbon source | Strain name W. cibaria GSKM06 |
| --- | --- |
| Inulin | – |
| D-melezitose | – |
| D-raffinose | – |
| Amidon (starch) | – |
| Glycogen | – |
| Xylitol | – |
| Gentiobiose | + |
| D-turanose | – |
| D-lyxose | – |
| D-tagatose | – |
| D-fucose | – |
| L-fucose | – |
| D-arabitol | – |
| L-arabitol | – |
| Potassium gluconate | + |
| Potassium 2-ketogluconate | – |
| Potassium 5-ketogluconate | – |

* Degradation: +, –

Experimental Example 1: Evaluation of Safety of *Weissella cibaria* GSKM06 (*W. cibaria* GSKM06)

1. Determination as to Presence of Hemolytic Activity

In order to evaluate the safety of the lactic acid bacteria of the present invention, the presence of hemolytic activity (α, β, γ-hemolysis) was determined. At this time, *Staphylococcus aureus* KCTC 3881 (Korean Collection for Type Cultures, Korea) having β-hemolysis activity was used as a positive control.

More specifically, each bacteria was seeded in a blood solid medium supplemented with 5% (v/v) defibrinated sheep blood and anaerobically cultured at 37° C. for 48 hours. Then, whether or not a clear zone was formed was determined and the results are shown in Table 2 below.

TABLE 2

| Strain | Hemolysis (α, β, γ) |
| --- | --- |
| *S. aureus* KCTC 3881 | β |
| *W. cibaria* GSKM06 | α |

The result of the test showed that the positive control *Staphylococcus aureus* strain produced a clear zone, whereas the GSKM06 strain, the lactic acid bacteria of the present invention, did not produce a clear zone.

Accordingly, it can be seen that the *Weissella cibaria* GSKM06 strain of the present invention have no hemolytic activity.

2. Determination as to Antibiotic Resistance

In order to evaluate the safety of the lactic acid bacteria of the present invention, presence of antibiotic resistance was determined. The antibiotic resistance was tested using M.I.C. Evaluator Strips (Oxoid, Cambridge, UK) with 15 antibiotic concentrations serially diluted by 1/2 in accordance with the European Food Safety Authority (EFSA, 2012) standards.

A total of eight antibiotics was used at concentrations shown in Table 3 above and LSM medium containing isoSensitest broth (Oxoid, UK) suggested by ISO and MRS agar (Oxoid, UK) at a ratio of 9:1 was used as a medium for determining the minimum inhibitory concentrations (MICs) of the lactic acid bacteria of the present invention. Whether or not antibiotic resistance was present was determined by seeding each lactic acid bacteria in the LSM medium, placing an antibiotic strip therein and culturing for 24 hours under anaerobic conditions at 37° C. The results are shown in Table 4 below.

TABLE 3

| Antibiotic | Concentration |
|---|---|
| Ampicillin [AMP] | 0.016-256 |
| Gentamicin [CN] | 0.016-256 |
| Kanamycin [K] | 0.016-256 |
| Streptomycin [S] | 0.064-1024 |
| Erythromycin [E] | 0.016-256 |
| Clindamycin [CD] | 0.016-256 |
| Tetracycline [TE] | 0.016-256 |
| Chloramphenicol [C] | 0.016-256 |

TABLE 4

| | | AMP | CN | K | S | E | CD | TE | C |
|---|---|---|---|---|---|---|---|---|---|
| ESFA (2012) | Lactobacillus obligate hetero-fermentative (Weissella sp.) | 2 | 16 | 32 | 64 | 1 | 1 | 8 | 4 |
| W. cibaria GSKM06 | | 0.38 | 1 | 48 | 48 | 0.25 | 0.75 | 1 | 4 |

The result of the test showed that the *Weissella cibaria* GSKM06 strain was resistant to kanamycin.

Meanwhile, whether or not the *Weissella cibaria* GSKM06 strain had antibiotic resistance-related genes was determined using the Resfinder 4.1 database based on the results of the whole genome analysis of the strain, whether or not the *Weissella cibaria* GSKM06 strain had mediating horizontal genes (plasmids, prophage and insertion sequence elements) highly related to lateral movement of genes were determined using the PlasmidFinder 2.0 analysis program (FIG. 1), and the results are shown in Tables 5 and 6 below. FIG. 1 shows the result of determination as to whether or not the lactic acid bacterium of the present invention, *Weissella cibaria* GSKM06 strain has mediating horizontal genes highly related to lateral transfer.

TABLE 5

| Strain name | Perfect Hits | Strict Hits | Loose Hits |
|---|---|---|---|
| W. cibaria GSKM06 | 0 | 2 | 138 |

* Perfect Hits: matches reference sequence
* Strict Hits: similarity within model
* Loose Hits: similarity outside of model

TABLE 6

| | Strain name W. cibaria GSKM06 |
|---|---|
| Aminoglycoside (22) | – |
| Beta-lactam (27) | – |
| Lincosamide (2) | – |
| Macrolide (8) | – |
| Phenicol (3) | – |
| Tetracycline (5) | – |
| Aldehydes (1) | – |
| Aminocyclitol (1) | – |
| Fluoroquinolone (3) | – |
| Folate pathway antagonist (2) | – |
| Fosfomycin (1) | – |
| Glycopeptide (2) | – |
| Nitroimidazole (1) | – |
| Oxazolidinone (1) | – |
| Peroxides (1) | – |
| Pleuromutilin (1) | – |
| Polymyxin (1) | – |
| Pseudomonic acid (1) | – |
| Quaternary ammonium compounds (1) | – |
| Rifamycin (2) | – |
| Steroid antibacterial (1) | – |
| Streptogramin a (4) | – |
| Streptogramin b (3) | – |
| Under_development (1) | – |

* ( ): the number of antibiotics in each class

The result of the test showed that the strain GSKM06 had no transfer between antibiotic resistance-related genes and antibiotic resistance.

This means that the GSKM06 strain of the present invention is a safe bacterium free of concerns about antibiotic resistance.

Experimental Example 2: Test for Pathogen Inhibition Efficacy of *Weissella cibaria* GSKM06 (*W. cibaria* GSKM06)

1. Evaluation (Qualitative Evaluation) of Ability of Lactic Acid Bacteria to Inhibit Local Immune Hypersensitivity Pathogenic Bacteria In order to qualitatively evaluate the inhibitory ability of the lactic acid bacteria of the present invention against pathogenic bacteria, an agar-well diffusion assay (Int. J. Infect. Dis., 2004, Vol. (8), p. 39-45) was performed. Indicator bacteria used herein are shown in Table 7 below.

TABLE 7

| Strain name | Related diseases/remarks |
|---|---|
| Streptococcus pneumoniae KCTC 5764 | The most common causative strain of community-acquired pneumonia |
| Moraxella catarrhalis KCCM 42706 | Harmful bacterium that may infect the respiratory tract, central nervous system and human joints |
| Haemophilus influenzae KCCM 42705 | Bacterium that causes extensive local and invasive infections, as well as bacteremia, pneumonia, epiglottitis, and acute bacterial meningitis |
| Staphylococcus aureus KCOM 1335 | Bacterium that causes pyogenic infection, resulting in systemic infections such as sepsis, pneumonia and meningitis, and eventually causing various diseases |
| Pseudomonas aeruginosa KCTC 22063 | Pseudomonas aeruginosa that produces green pus, causing pneumonia, osteoarthritis, and soft tissue |

More specifically, the *Weissella cibaria* GSKM06 strain of the present invention was cultured in MRS broth under aerobic conditions at 37° C. for 18 hours. The activated strain was centrifuged and then the supernatant, from which the pellet was removed, was filtered through a 0.22 μm filter, and the result was used as an antibacterial substance. When only the pellet is removed, a small amount of bacteria remaining in the supernatant may cause formation of a lawn on the agar plate. Therefore, the bacteria was filtered and then used for the inhibitory efficacy test.

The antibacterial activity against *S. pneumoniae* KCTC5764 strain known as Pneumococcus was evaluated as follows. The culture medium activated with BHI broth overnight was diluted 100 times, inoculated into BHI agar, poured onto a plate and then dried. The plate was completely dried and wells were formed using a 6 mm biopsy punch (Kai Medical, Germany), and 100 μl of the supernatant of *Weissella cibaria* GSKM06 strain was seeded in each well. As positive controls, a disc containing 10 μl of ampicillin, one of the antibiotics, and MRS medium were used. After incubation at 37° C. for 24 hours, the turbidity level of the agar plate was visually observed to determine whether or not the bacteria had grown well on the plate, and at the same time, whether or not a transparent ring was formed by ungrown bacteria around the well was determined. The results are shown in Table 8 below.

TABLE 8

| Inhibition zone (mm) | |
| --- | --- |
| Strain name | W. cibaria GSKM06 |
| S. pneumoniae KCTC 5764 | 0 |
| H. influenzae KCCM 42705 | 0 |
| M. catarrhalis KCCM 42706 | 3 |
| S. aureus KCTC 1335 | 0 |
| P. aeruginosa KCTC 1182 | 0 |

The result of the test showed the *Weissella cibaria* GSKM06 strain had the highest inhibitory activity against the *Moraxella catarrhalis* KCCM42706 strain, but had no inhibitory activity against other activated harmful bacteria.
2. Evaluation (Quantitative Evaluation) of Ability of Lactic Acid Bacteria to Inhibit Local Immune Hypersensitivity Pathogenic Bacteria A microtiter plate assay (Food Chemistry, 2008, 111(4), p. 1069-1074) was performed to quantitatively evaluate the inhibitory ability of the lactic acid bacteria of the present invention against local immune hypersensitivity pathogens. 5 kinds of harmful bacteria that increased in the body due to local hypersensitivity reactions among pathogenic bacteria were selected as indicator bacteria, and the strains used herein were the same as those used for qualitative evaluation as shown in Table 7.

More specifically, the *Weissella cibaria* GSKM06 strain was cultured in MRS broth under aerobic conditions at 37° C. for 18 hours. The active strain was centrifuged at 15,000 rpm for 5 minutes, the supernatant was isolated from the strain, the pH of the isolated supernatant was adjusted to 6.5 to 7, and the supernatant, from which the pellet was removed, was filtered through a 0.22 μm filter, which was used as an antibacterial substance.

200 μl of BHI liquid medium (Difco, USA) was added to a 96-well plate and the plate was inoculated with 1% activated *S. pneumoniae* KCTC5764. 10 μl of the supernatant of the strain was added to each well inoculated with the indicator bacteria, and incubated at 37° C. for 24 hours under anaerobic conditions, and the O.D. was measured at 600 nm. Then, the antibacterial activity was determined by calculation in accordance with an equation and the results are shown in Table 9 below. Five indicator bacteria were tested in the same manner except that an indicator titration medium was changed.

Bacterial activity (inhibition, %) =

$$\left[1 - RLU_{selection\ bacterium}/RLU_{indicator\ bacterium}\right] * 100$$

TABLE 9

| Strain name | W. cibaria GSKM06 |
| --- | --- |
| S. pneumoniae KCTC 5764 | 0 |
| H. influenzae KCCM 42705 | 0 |
| M. catarrhalis KCCM 42706 | 14.41 ± 0.01 |
| S. aureus KCTC 1335 | 2.29 ± 0.01 |
| P. aeruginosa KCTC 1182 | 3.11 ± 0.01 |

* Bacterial activity (inhibition, %)

The result of the test showed that the *Weissella cibaria* GSKM06 strain had the highest inhibitory ability against the *Moraxella catarrhalis* 42706 strain, similar to the above.

Experimental Example 3: Test of Inhibitory
Activity *Weissella cibaria* GSKM06 (*W. cibaria*
GSKM06) Against Macrophage Inflammation 1. Nitric Oxide Assay (NO Assay)

In order to evaluate the anti-inflammatory activity of the lactic acid bacteria of the present invention, changes in nitrogen monoxide due to treatment with the lactic acid bacteria were measured.

More specifically, MH-S cells, which are mouse lung macrophages, were seeded in RPMI1640 supplemented with 10% FBS at 37° C. in the presence of 5% $CO_2$ at a density of 50,000 cells/well in a 24-well plate, followed by culturing for 24 hours. The supernatant was removed, 500 ng/ml of LPS and 10 ng/ml of IFN-γ were added to the RPMI1640 medium, and then the medium was treated with the *Weissella cibaria* GSKM06 strain at $1 \times 10^7$ CFU/ml and cultured for 24 hours. Then, the supernatant was collected and NO secretion was measured using a Griess reagent system (Promega).

The result of the test showed that the production of nitric oxide, which was increased by the treatment with LPS+IFN-γ, was inhibited by treatment with the *Weissella cibaria* GSKM06 strain. In particular, it can be seen that the *Weissella cibaria* GSKM06 strain is highly effective in inhibiting production of nitric oxide that was increased by treatment with LPS+IFN-γ (FIG. 2). FIG. 2 shows the result of the test of the ability of the lactic acid bacteria (*W. cibaria* GSKM06) according to the present invention to inhibit nitric oxide (NO) production.
2. Test of Inhibitory Activity Against Mast Cell Line Degranulation (β-Hexosaminidase Assay)

RBL-2H3 cells, which are rat basophil leukemia cells, were cultured in EMEM supplemented with 15% heat-inactivated FBS on a 12-well plate at a density of 200,000 cells/well at 37° C. in the presence of 5% $CO_2$ for 24 hours. The supernatant was removed, the cells were incubated in an EMEM medium containing 0.5 mg/mL anti-DNP IgE for 16 hours, the supernatant was removed from the cells, and the EMEM medium was treated with the *Weissella cibaria* GSKM06 strain at a concentration of $1\times10^8$ CFU/mL for 2 hours, followed by incubation.

After incubation, the cells were washed twice with Siraganian buffer and 200 ng/ml of DNP-HAS was added to the Siraganian buffer, followed by allowing to react for 1 hour. After the reaction was terminated at 4° C., 40 μl of the supernatant was added to a 96-well plate, and 40 μl of 1 mM P-nitrophenyl-acetyl-β-D-glucosaminide was added thereto, followed by allowing to react at 37° C. for 1 hour. 0.1M $Na_2CO_3$ was added to the resulting product, all reactions were terminated, and the absorbance was measured at 405 nm with a microplate reader.

Figure 3:
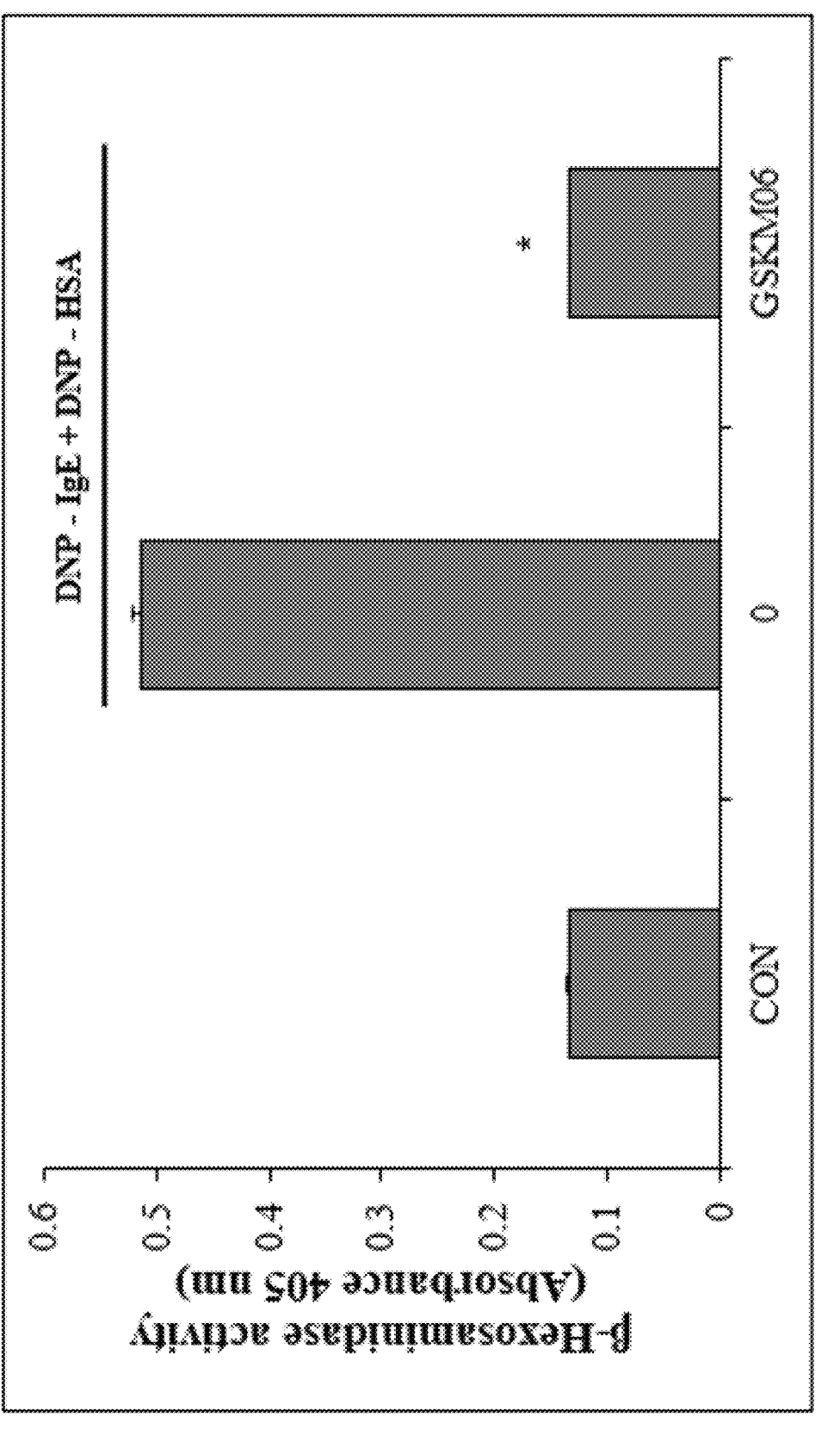
FIG. 3 shows the result of determination as to the ability of the lactic acid bacteria (*W. cibaria* GSKM06) according to the present invention to inhibit β-hexosaminidase production.

The result of the test showed that the production of β-hexosaminidase, which was enhanced by treatment with DNP-IgE+DNP-HSA, was effectively inhibited by treatment with the *Weissella cibaria* GSKM06 strain (FIG. 3). FIG. 3 shows the result of determination as to the ability of lactic acid bacteria (*W. cibaria* GSKM06) according to the present invention to inhibit β-hexosaminidase production.

Experimental Example 4: Test of Airway Adhesion Ability of *Weissella cibaria* GSKM06 (*W. cibaria* GSKM06)

In order to evaluate the adhesion ability in the airway of the lactic acid bacteria of the present invention, the adhesion ability (Infect Immun 45:534-536, 1984.) was investigated using BEAS-2B cells, which are human bronchial epithelial cells.

More specifically, human bronchial epithelial cells, BEAS-2B cells, were subcultured in a $CO_2$ incubator in M199 medium supplemented with 10% FBS (2 mM L-glutamine, 2.5 μg/ml insulin, 361 ng/ml hydrocortisone, 20 ng/ml EGF and 1% antibiotics). The cells were incubated at a density of $1\times10^5$ cells/well in a 24-well plate for 24 hours and were washed twice with PBS, and each $1\times10^8$ CFU/ml of *Weissella cibaria* GSKM06 strain was added thereto, followed by incubation at 37° C., in a % $CO_2$ incubator for 15, 30 and 60 minutes.

Then, the cells were washed three times with PBS, fixed with methanol, subjected to Giemsa staining for 30 minutes, washed again with PBS, and dried in air, and the adhesion ability to each cell was investigated using an optical microscope.

Figure 4:
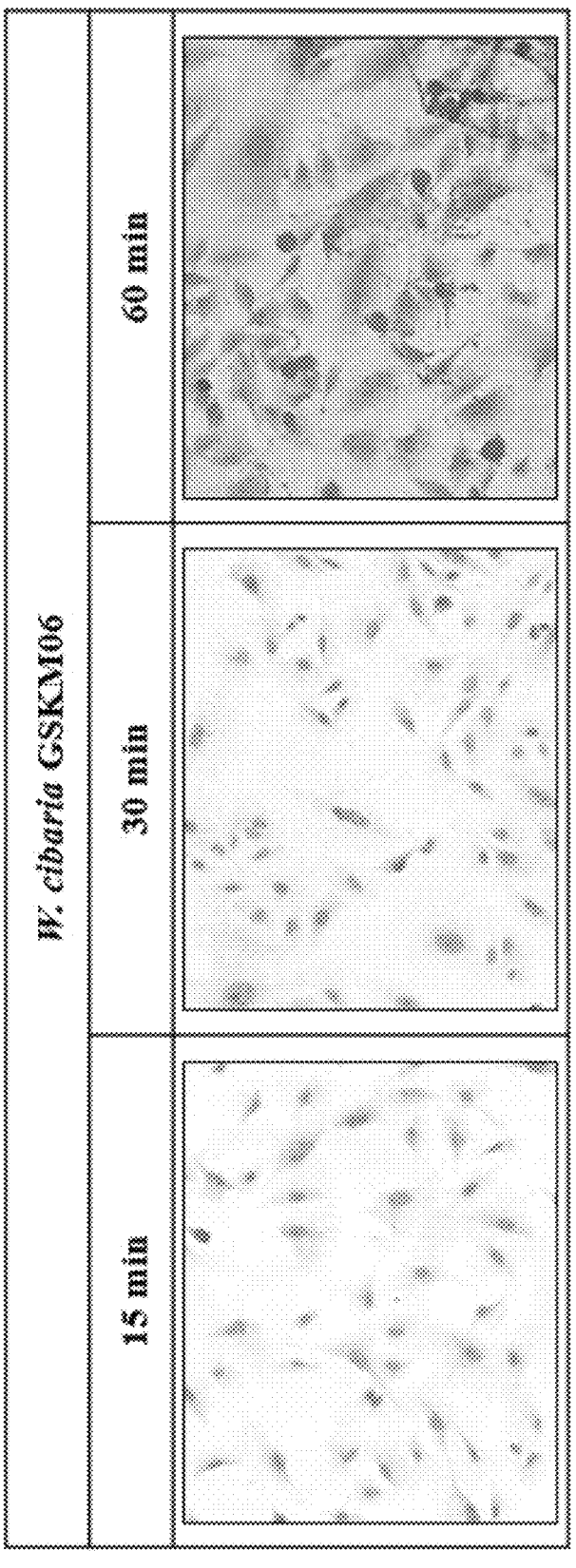
FIG. 4 shows the result of determination of the airway adhesion ability of the lactic acid bacteria (*W. cibaria* GSKM06) according to the present invention.

The result of the test showed that the *Weissella cibaria* GSKM06 strain was attached to the airways in BEAS-2B cells at 60 minutes among 15, 30, and 60 minutes (FIG. 4). FIG. 4 shows the result of determination as to the airway adhesion ability of lactic acid bacteria (*W. cibaria* GSKM06) according to the present invention.

Experimental Example 5: Evaluation of Local Hypersensitivity Amelioration Efficacy of *Weissella cibaria* GSKM06 (*W. cibaria* GSKM06) Using Animal Model The animals used herein were 5-week-old male BALB/c mice. After a 1-week acclimatization period, on Day 0 and Day 14 of the test, an OVA mixture [20 μg OVA (Albumin from chicken egg white) lyophilized powder, Sigma)+30 μl PBS+50 μl Inject Alum (Thermo)] was subcutaneously injected into an induction group (S.C), and the same amount of PBS was injected into a normal control group.

The mice were sensitized by injection of the antigen and the same antigen was brought into contact through the airway of the mice, to cause an intensive inflammatory reaction in the bronchi and lungs thereby induce asthma, which is hypersensitivity.

As shown in Table 10 below, the experimental group was divided into three groups, and the test substance was administered (orally administered) thereto until 15 to 42 days (4 weeks) from the start of the test. Before the end of 4-week administration of lactic acid bacteria, PBS containing 3% OVA was aerosolized through a nebulizer in a closed separate chamber for 20 minutes daily over 5 days.

The result was allowed to stand overnight and then an autopsy was performed on the day 43. After the final administration of the test substance, the mice were fasted overnight (for 4 to 6 hours) and all mice were subjected to cardiac blood collection under $CO_2$ anesthesia immediately before autopsy. The mice were euthanized by cervical dislocation and organs were collected from all test groups after laparotomy. For autopsy items, after anesthesia, blood was collected from the heart, serum was isolated therefrom, and target organs such as airways and lungs were removed and frozen.

TABLE 10

| | Whether or not asthma is induced | Test substance | Number of lactic acid bacteria | Administration on route | Dose | Number of animals |
|---|---|---|---|---|---|---|
| G1 | X | Control (D.W) | | Oral administration | 0.1 ml | 9 |
| G2 | O | Asthma control (D.W) | | | | 9 |
| G3 | O | GSKM06 | $10^9$ CFU/ g | | | 9 |
| | | | | | | 27, total |

Figure 5:
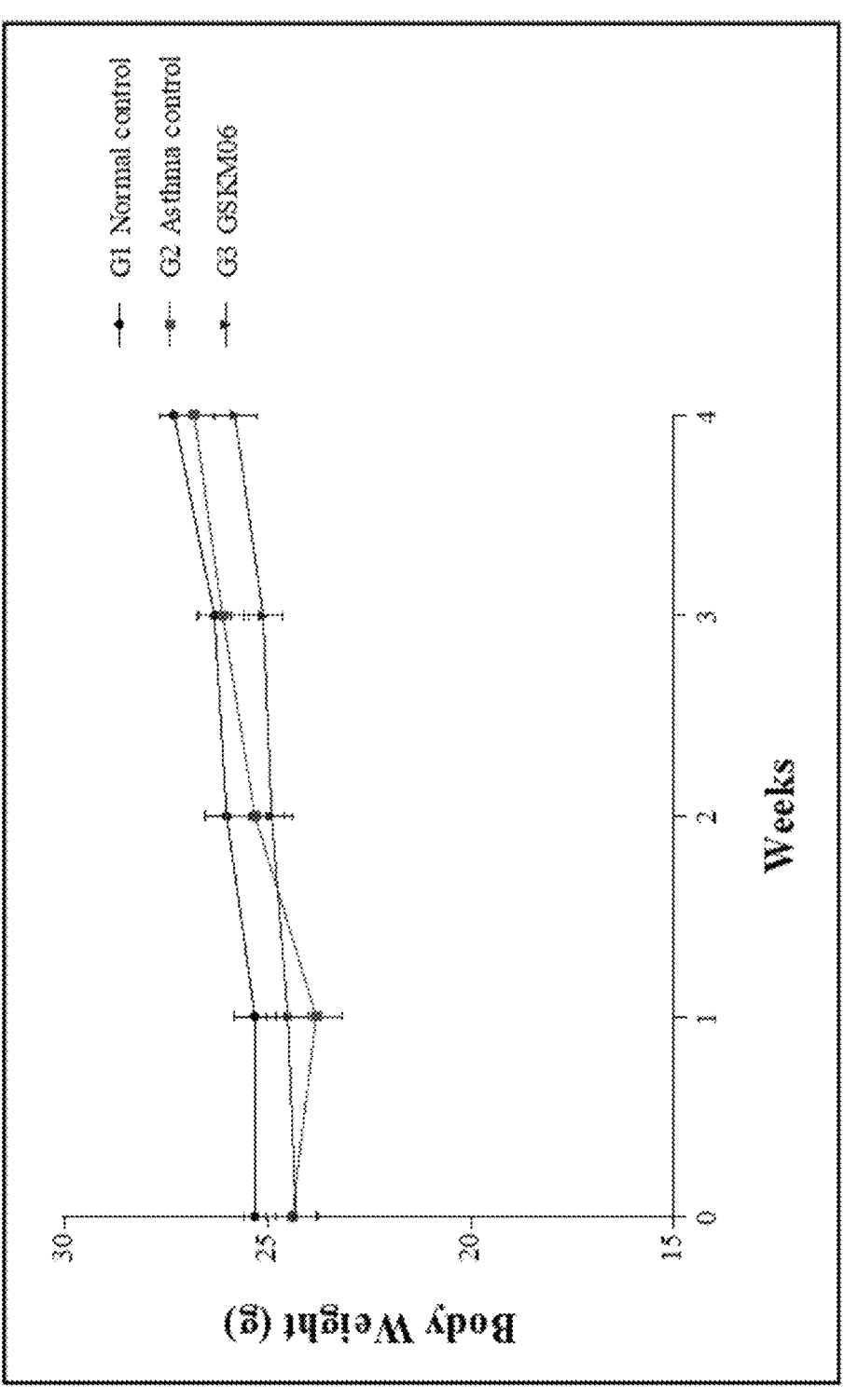
FIG. 5 shows the result of determination as to the effect of administration of the present invention lactic acid bacteria (*W. cibaria* GSKM06) on weight change of the mouse.

The result of the test showed that there was no significant difference in body weight between the group (G3) administered with the *Weissella cibaria* GSKM06 strain, and G1 (control) and G2 (asthma control). This indicates that the lactic acid bacteria according to the present invention did not significantly affect body weight change (FIG. 5). FIG. 5 shows the result of determination as to the effect of administration of the present invention lactic acid bacteria (*W. cibaria* GSKM06) on change of mouse weight.

Experimental Example 6: Analysis of Local Hypersensitivity and Inflammation Amelioration Efficacy of *Weissella cibaria* GSKM06 (*W. cibaria* GSKM06) Using Animal Models Inflammatory cells (total inflammatory cells) involved in the allergic inflammatory response in the bronchus includes mast cells, neutrophils, eosinophils, macrophages, and lymphocytes, and secrete cytokines, growth factors, and decomposition enzymes, thus playing an essential role in defense against inflammation and infection.

Eosinophils contain inflammatory proteins, directly damage airway epithelial cells, increase airway hypersensitivity, and cause mast cell degranulation. In addition, it contains leukotriene, thus increasing airway constriction and vascular permeability. Mast cells mature in the mucous membrane of the airway, and release histamine and leukotrienes present in mast cells when an allergen binds to IgE.

In addition, eosinophils are involved in the production of IL-1, 2, 3, 4, 5, IFN-γ, and TNF-α and mediate allergic and chronic inflammation. Histamine and leukotrienes are secreted from mast cells during the initial allergic reaction, which are used as indicators of the inflammatory response. T cells (T lymphocytes) are lymphocytes responsible for antigen-specific adaptive immunity, and are activated into mature effector T cells when antigens invade the body, to initiate adaptive immunity, which can be used as an inflammatory response indicator.

B cells (B lymphocytes) produce antibodies in lymphocytes and are activated during an allergic inflammatory response to increase production of IgE, which can be used as an indicator of allergic inflammatory responses.

Accordingly, experiments were performed on various factors in order to evaluate the effects of ameliorating the local hypersensitivity reaction and inflammation of the *Weissella cibaria* GSKM06 strain.

1. Enzyme-Linked Immunosorbent Assay (ELISA); IgE

IgE is activated in airway epithelial cells of patients with allergic inflammation and chronic inflammation, and at this time, the cells secrete a large amount of inflammatory mediators. Inflammatory mediators mainly activate alveolar macrophages and neutrophils, and release proteolytic enzymes, resulting in lung damage along with reactive oxygen species. Therefore, this experiment was performed with the goal of evaluating the efficacy of asthma amelioration (immunity amelioration or normalization) and inflammation amelioration by administration of lactic acid bacteria in immune hypersensitivity (asthma)-induced animal model using OVA.

More specifically, blood was collected from the heart of each subject, the blood was centrifuged twice at 10,000 rpm and 4° C. for 5 minutes, and only the supernatant, serum, was used for analysis. The separated serum was analyzed using an ELISA assay in accordance with the protocol in the IgE (Abcam, UK) kit.

Figure 6:
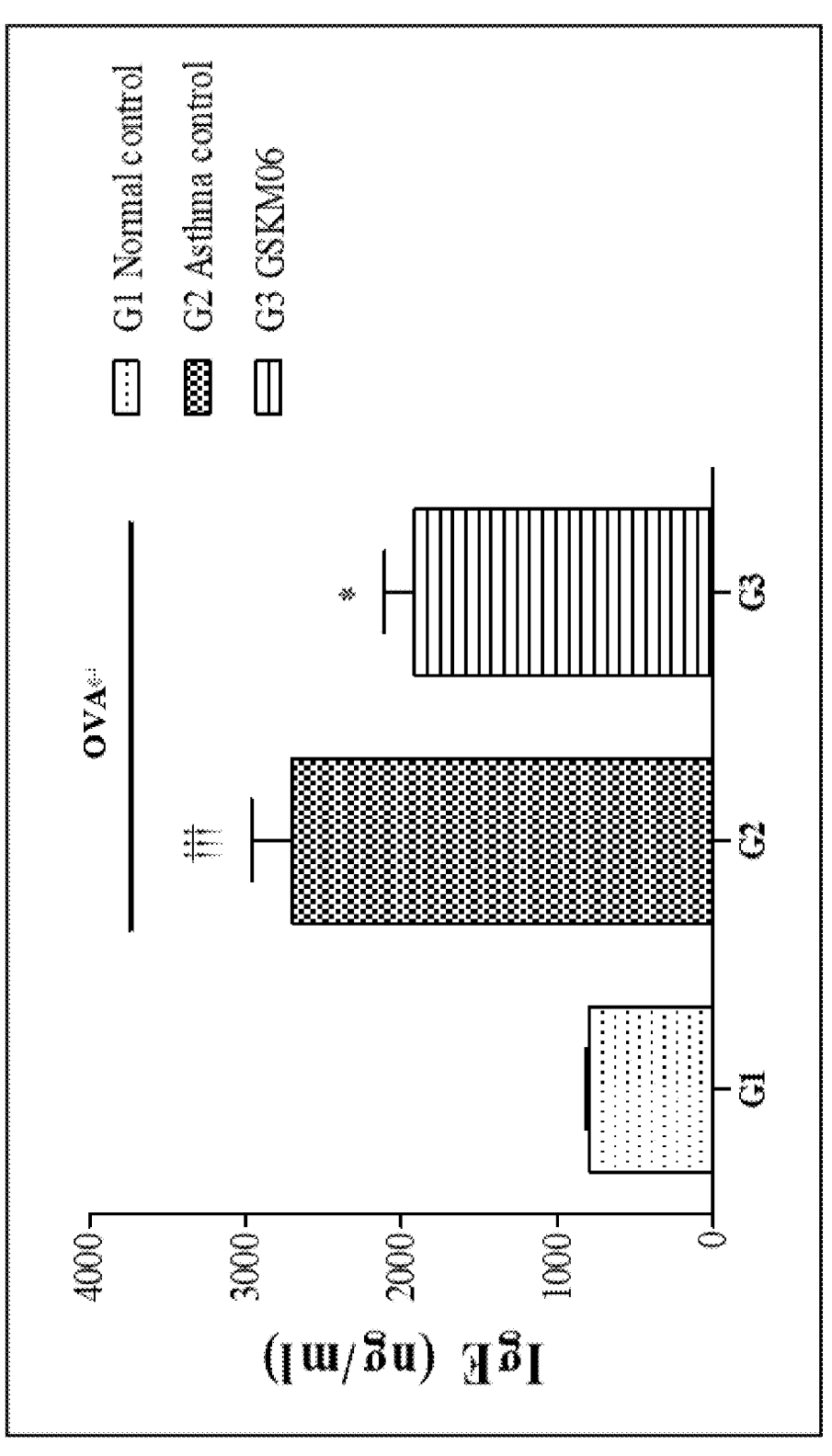
FIG. 6 shows the result of determination as to the effect of administration of the lactic acid bacteria according to the present invention (*W. cibaria* GSKM06) on reduction of IgE in serum.
Figure 7:
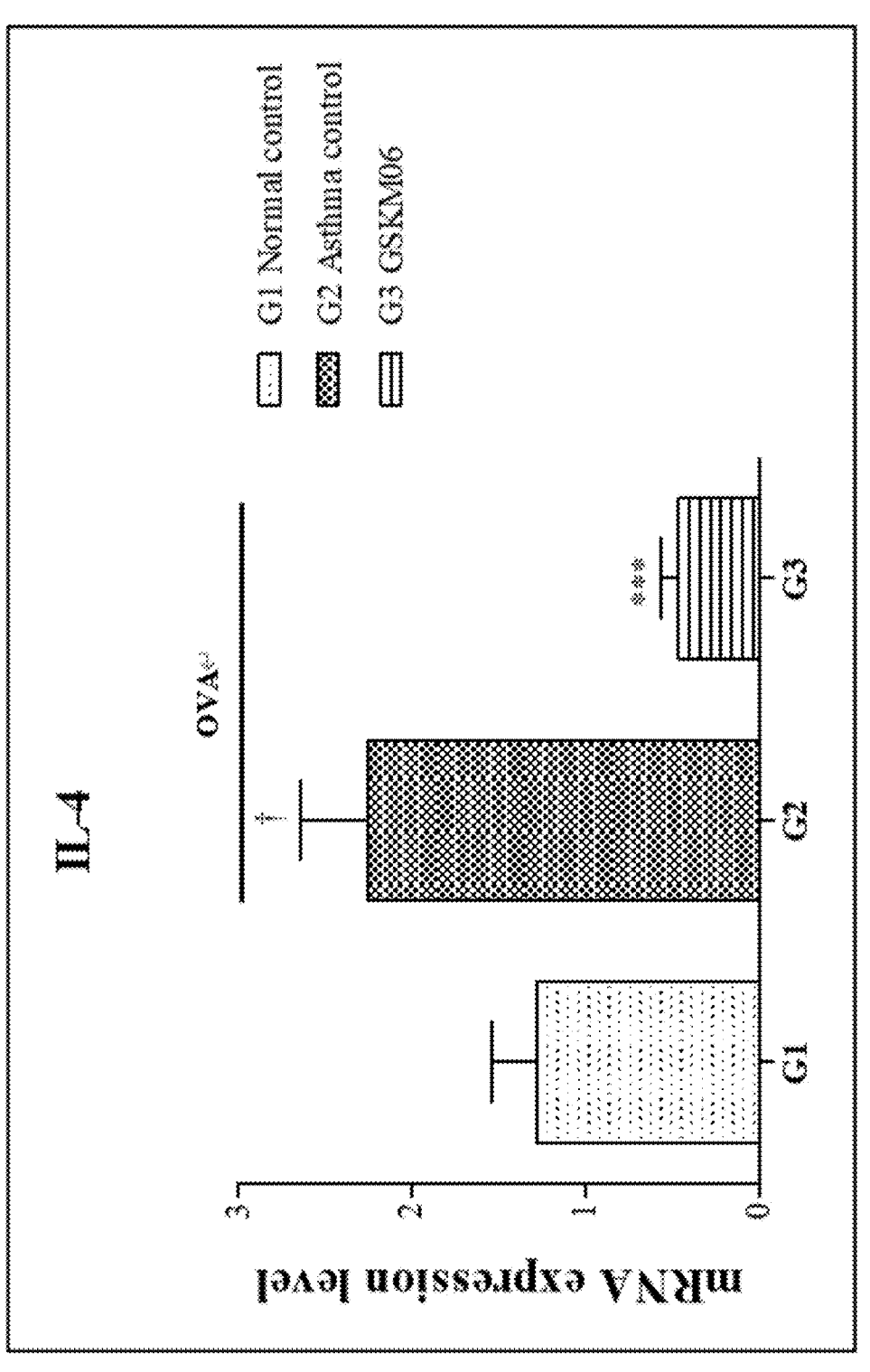
FIG. 7 shows the result of determination as to the effect of administration of the lactic acid bacteria according to the present invention (*W. cibaria* GSKM06) to the airway inflammation-induced group on reduction of IL-4.
Figure 8:
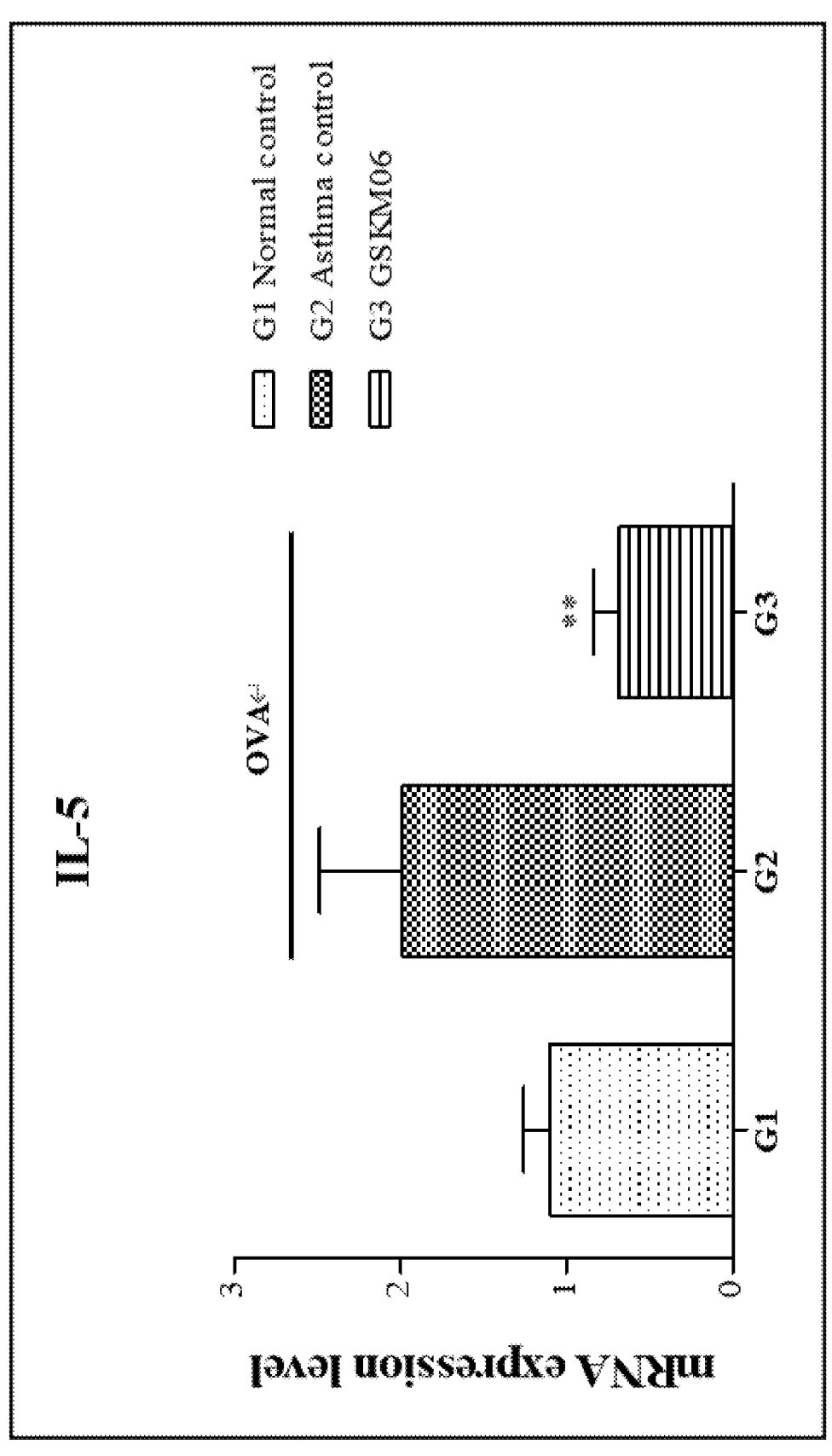
FIG. 8 shows the result of determination as to the effect of administration of the lactic acid bacteria according to the present invention (*W. cibaria* GSKM06) to the airway inflammation-induced group on reduction of IL-5.
Figure 9:
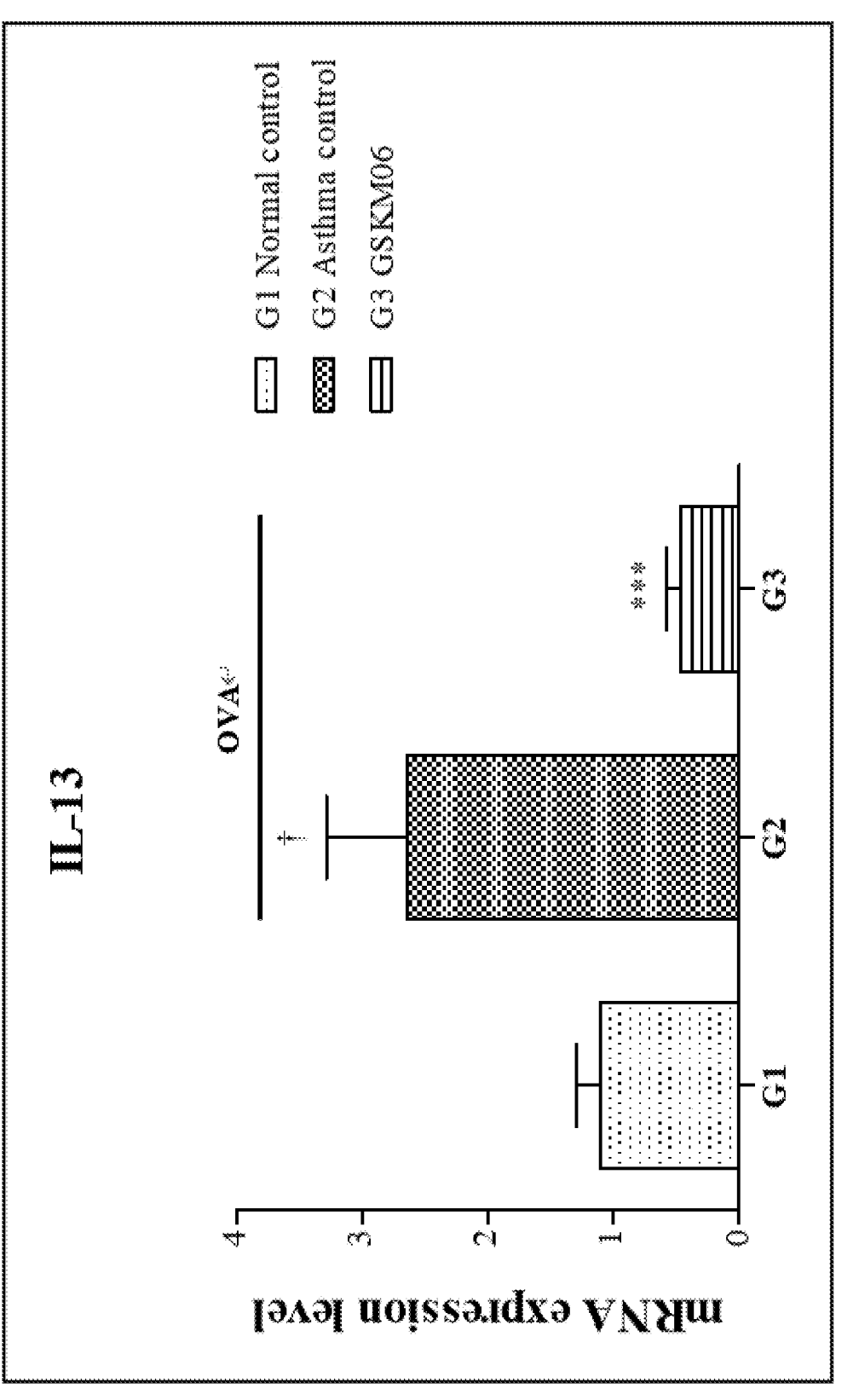
FIG. 9 shows the result of determination as to the effect of administration of the lactic acid bacteria according to the present invention (*W. cibaria* GSKM06) to the airway inflammation-induced group on reduction of IL-13.
Figure 10:
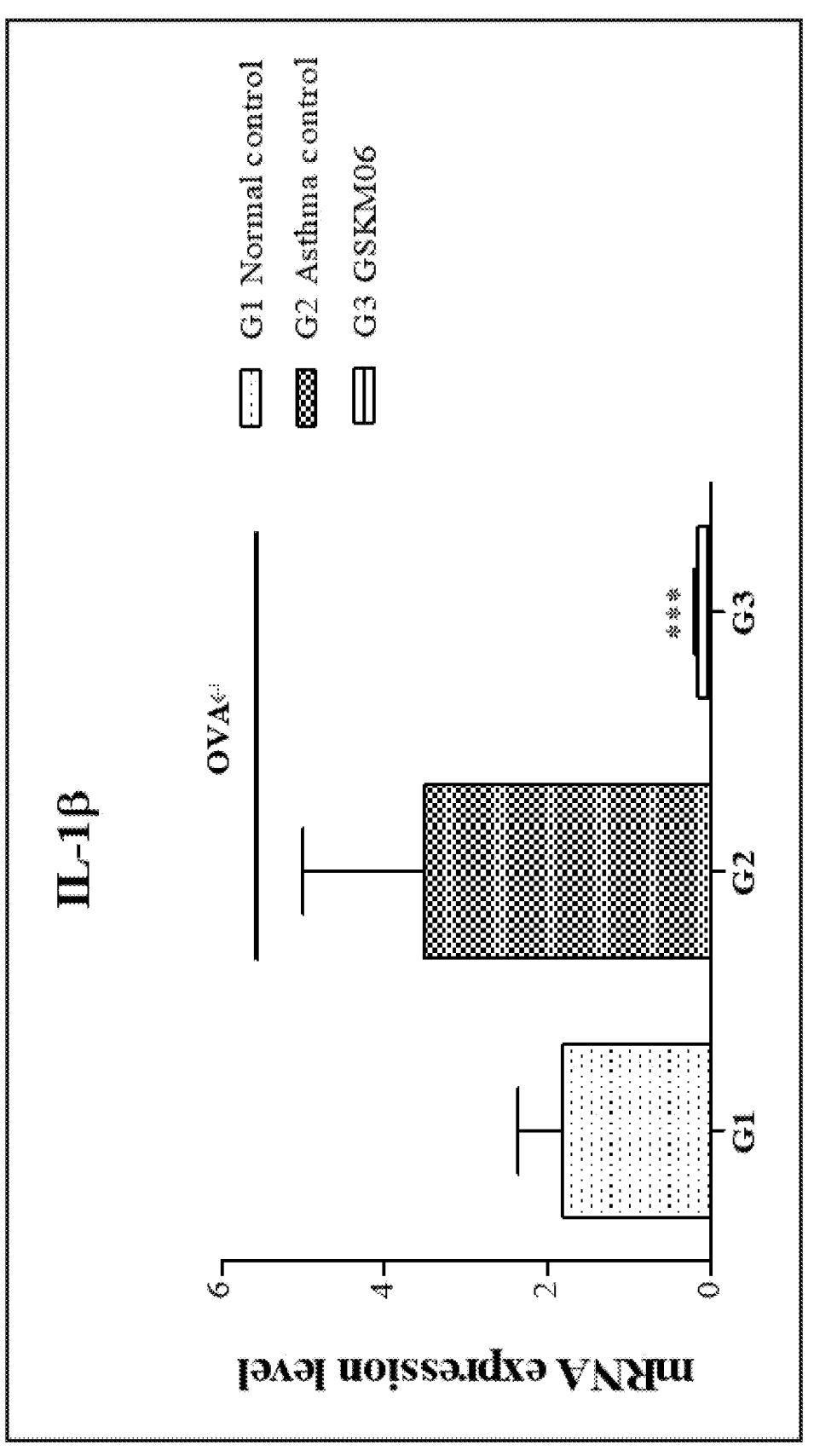
FIG. 10 shows the result of determination as to the effect of administration of the lactic acid bacteria according to the present invention (*W. cibaria* GSKM06) to the airway inflammation-induced group on reduction of IL-1B.
Figure 11:
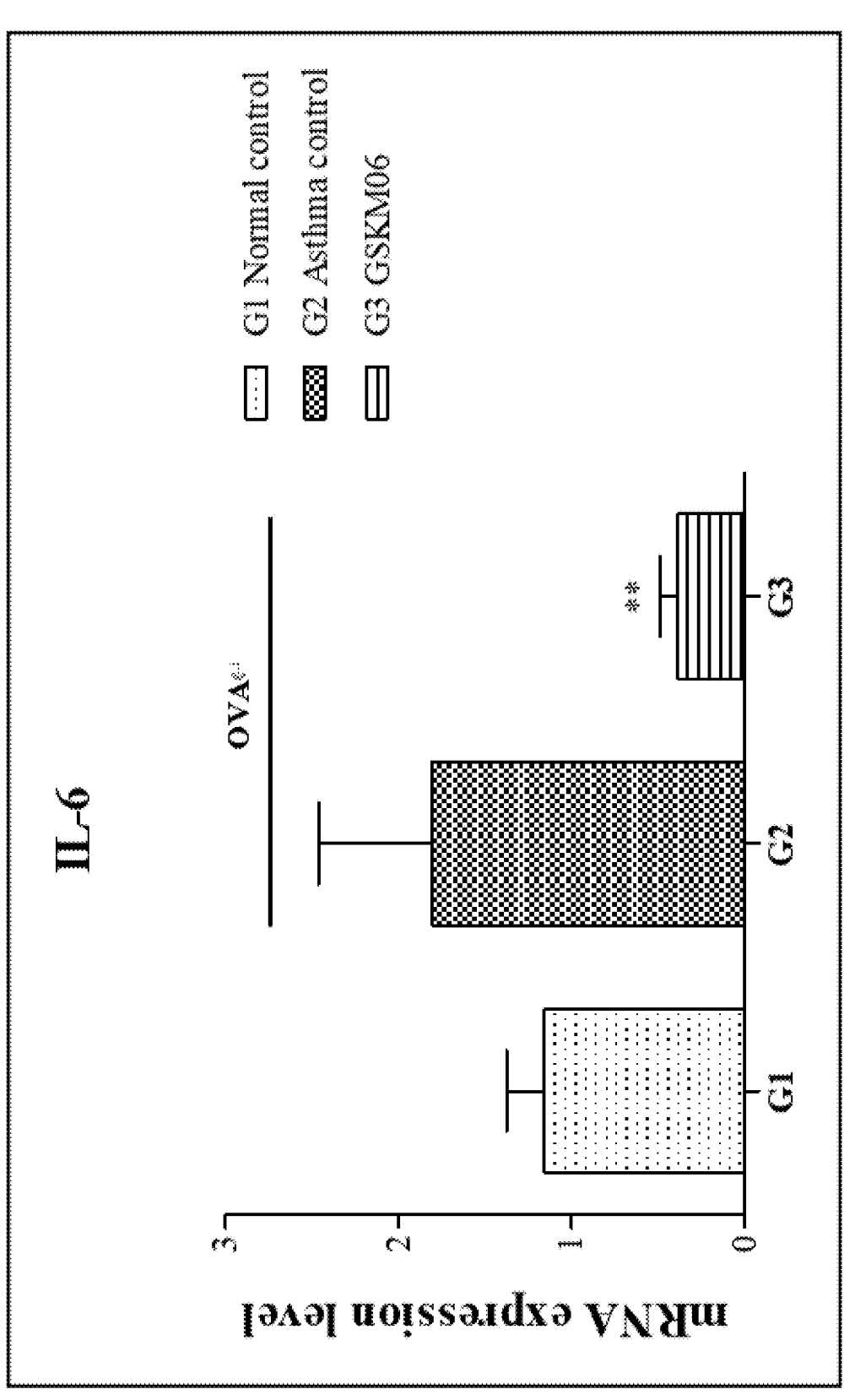
FIG. 11 shows the result of determination as to the effect of administration of the lactic acid bacteria according to the present invention (*W. cibaria* GSKM06) to the airway inflammation-induced group on reduction of IL-6.
Figure 12:
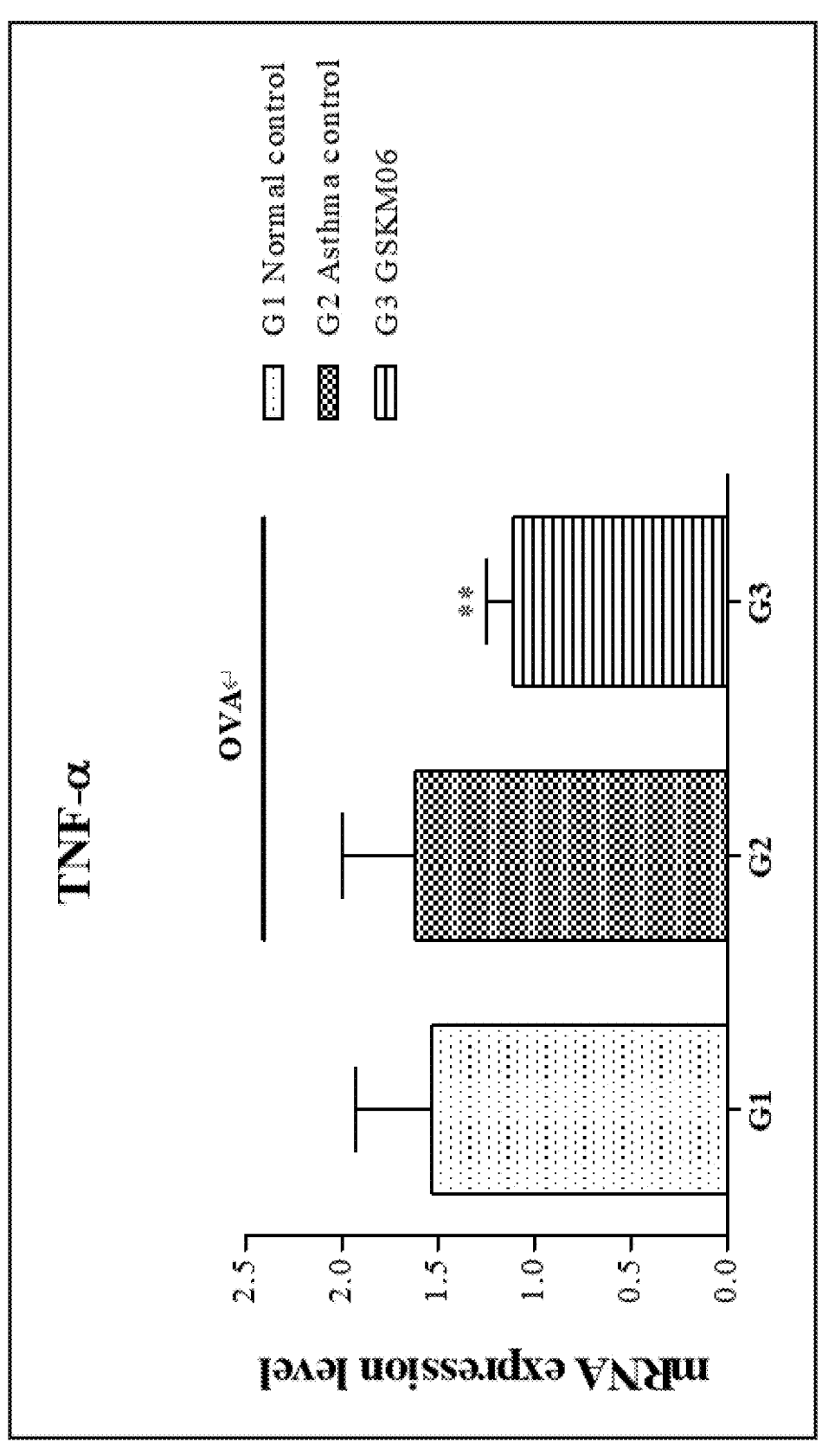

The result of the test showed that G2 (asthma control) exhibited significantly increased IgE compared to G1 (control), which indicates that asthma was induced. The group (G3) administered the *Weissella cibaria* GSKM06 strain effectively reduced an IgE level increased by the induction of asthma (FIG. 6). FIG. 6 shows the result of determination as to the effect of reducing the IgE in serum by the administration of lactic acid bacteria according to the present invention (*W. cibaria* GSKM06).

These results showed that the administration of *Weissella cibaria* GSKM06 strain is effective in reducing the secretion of inflammatory mediators caused by allergens.

2. PCR (Lung Tissue); IL-4, IL-5, IL-13, IL-1β, IL-6, TNF-α

Th2 cells induce allergic airway inflammation by stimulating the secretion of cytokines such as IL-1β, 4, 5, 6, and 13. IL-4, along with IL-13, is involved in Th2 cell differentiation, induces an eosinophilic inflammatory response in lung tissue, and activates the Th2 transcription factor GATA-3 in this process. In addition, IL-4 is involved in mucus and secretion (dimorphism of goblet cells), airway fibrosis, and switching from IgG to IgE.

IL-5 is a major cytokine involved in eosinophilic inflammation and promotes differentiation into eosinophils from the bone marrow. IL-13 is involved in Th2 cell differentiation, B cell activation, mucus hyperplasia, dimorphism of goblet cells, and basement membrane thickness increase. In addition, IL-13 establishes an environment enabling eosinophils to survive in the airway. IL-1B is secreted by severe inflammation and is involved in macrophage activation and induction of neutrophilic inflammatory responses.

IL-6 is also involved in eosinophil migration and survival. IL-6 promotes an inflammatory response, is involved in an immune response regulated by Th2 cells and Th17 cells, and is increased in sputum and blood of chronic inflammatory patients. TNF-α is secreted in macrophages and airway epithelial cells activated by chronic inflammation, and causes persistent inflammation. Therefore, in this experiment, PCR was performed with the goal of evaluating the change in cytokine levels in the asthma-induced experimental group by administration of lactic acid bacteria.

To this end, qRT-PCR was performed to determine the expression levels of inflammatory mediators such as inflammatory cytokines in lung tissues extracted from mice in all experimental groups. More specifically, total RNA was isolated using a lung tissue RIboEx solution. The concentration of the isolated RNA was assayed and then oligo-(dT) primer, dNTP mixture, RT premix & master mix were added to the total RNA and reacted to synthesize cDNA. In order to determine the efficacy of the extract, qRT-PCR was performed using the target markers shown in Table 11 below.

TABLE 11

| Target gene | | Sequence | Annealing Tm. |
|---|---|---|---|
| IL-4 | (F) | CCCCAGCTAGTTGTCATCCTG | 55° C. |
| | (R) | CAAGTGATTTTTGTCGCATCCG | |
| IL-5 | (F) | GGCTGGCCTCAAACTGGTAA | 60° C. |
| | (R) | CCCTGATGCAACGAAGAGGA | |
| IL-13 | (F) | CCTGGCTCTTGCTTGCCTT | 60° C. |
| | (R) | GGTCTTGTGTGATGTTGCTCA | |
| IL-1β | (F) | AGTTGACGGACCCCAAA | 55° C. |
| | (R) | TCTTGTTGATGTGCTGCTG | |
| IL-6 | (R) | AGGCATAACGCACTAGGTTT | 55° C. |
| | (F) | ACAGAAGGAGTGGCTAAGGA | |

TABLE 11-continued

| Target gene | Sequence | Annealing Tm. |
|---|---|---|
| TNF-α | (F) CCTGTAGCCCACGTCGTAG<br>(R) GGGAGTAGACAAGGTACAACCC | 60° C. |

The result of the test showed that G2 (asthma control) exhibited increased levels of IL-4, IL-5, IL-1β, IL-6, TNF-α, and IL-13, compared to G1 (control), which indicates that asthma was induced. The levels of IL-4, IL-5, IL-1β, IL-6, TNF-α, and IL-13 increased by induction of asthma were significantly decreased in the *Weissella cibaria* GSKM06 strain-administered group (G3) (FIGS. 7 to 12). FIGS. 7 to 12 show the reduction efficacy of IL-4, IL-5, IL-1β, IL-6, TNF-α, and IL-13 in the airway inflammation-induced group by administration of the lactic acid bacteria according to the present invention (*W. cibaria* GSKM06).

The results showing that the levels of inflammatory mediators were reduced overall by the *Weissella cibaria* GSKM06 strain mean that the *Weissella cibaria* GSKM06 strain has effects of ameliorating asthma, which is one form of immune hypersensitivity, eliminating immune hypersensitivity, and ameliorating inflammation caused by immune hypersensitivity.

As apparent from the foregoing, the strain according to the present invention has no toxicity to the human body and thus is safe, and has excellent physiological activities such as suppression of inflammatory reactions as well as immunomodulatory effects, thus being useful as a substance to treat immune hypersensitivity (allergic diseases such as skin, asthma and rhinitis), normalize immunity, and prevent, ameliorate or treat inflammatory diseases.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

ACCESSION NUMBER

Name of depository organization: Korea Research Institute of Bioscience and Biotechnology Biological Resources Center (KCTC)
Accession number: KCTC15129BP
Deposition date: 20221011

What is claimed is:

1. A method for treating asthma, the method comprising administering *Weissella cibaria* GSKM06 strain having the accession number of KCTC15129BP to a subject in need thereof.

2. The method according to claim 1, wherein the *Weissella cibaria* GSKM06 strain is selected from viable cells, dead cells, cell cultures, and strain extracts of *Weissella cibaria* GSKM06.

* * * * *